United States Patent [19]
Bird et al.

[11] Patent Number: 5,910,632
[45] Date of Patent: Jun. 8, 1999

[54] DNA ENCODING A PECTIN ESTERASE, CELLS AND PLANTS DERIVED THEREFROM

[75] Inventors: Colin Roger Bird, Bracknell; Brett Eric Burridge, Kegworth; Gregory Alan Tucker, Shepshed, all of United Kingdom; Jianliang Zhang, Gainesville, Fla.

[73] Assignee: Zeneca Limited, London, United Kingdom

[21] Appl. No.: 08/693,243

[22] PCT Filed: Feb. 22, 1995

[86] PCT No.: PCT/GB95/00367

§ 371 Date: Dec. 10, 1996

§ 102(e) Date: Dec. 10, 1996

[87] PCT Pub. No.: WO95/23227

PCT Pub. Date: Aug. 31, 1995

[30] Foreign Application Priority Data

Feb. 23, 1994 [GB] United Kingdom .................... 9403406

[51] Int. Cl.$^6$ .............................. C12N 5/10; C12N 15/63; C07H 21/04
[52] U.S. Cl. .......................... 800/298; 435/419; 435/423; 435/320.1; 536/23.2
[58] Field of Search ...................................... 435/410, 423, 435/320.1, 196, 197, 419; 536/23.2; 800/298

[56] References Cited

PUBLICATIONS

Harriman, R.W. et al. "Identification and characterization of three pectin methylesterase genes in tomato" Plant Physiology (May, 1990), vol. 93, No. 1 Suppl., p. 44, Abstract 249.

Ticker et al: "Purification and changes in activities of tomato pectinesterase isoenzymes", J. Sci. Food Agric., vol. 33, 1982, pp. 396–1982.

Hall et al: "Antisense inhibition of pectin esterase gene expression in transgenic tomatoes", The Plant J., vol. 3, 1993, pp. 121–129.

Harriman et al: "Molecular cloning of tomato pectin methylesterase gene and its expression in Rutgers, ripening inhibitor, nonripening and never ripe tomato fruits", Plant Physiol., vol. 97, 1991, pp. 80–87.

Markovic et al: "Tomato and Aspergillus niger pectinesterases", Protein Seq. Data Anal., vol. 3, 1990, pp. 513–515.

*Primary Examiner*—Kawai Lau
*Attorney, Agent, or Firm*—Pillsbury Madison & Sutro, LLP

[57] ABSTRACT

The invention provides DNA homologous to a DNA sequence which encodes a pectin esterase isoenzyme. Such DNA is incorporated into DNA constructs which are transformed into plants to increase or decrease expression of the related gene. This provides a method for modifying the phenotypic characteristics of plants, particularly fruit-ripening characteristics.

9 Claims, No Drawings

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (vi) ORIGINAL SOURCE:
      (A) ORGANISM: N-TERMINAL OF PE3

(xi) SEQUENCE DESCRIPTION: SEQ ID NO: 1:

Glu Asp Pro Tyr Arg Tyr Phe Asp Trp Xaa Val Thr
1               5                   10

(2) INFORMATION FOR SEQ ID NO: 2:

(i) SEQUENCE CHARACTERISTICS:
      (A) LENGTH: 814 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: 5' END PE3

(xi) SEQUENCE DESCRIPTION: SEQ ID NO: 2:

```
GAATTCGGAA ATATGTTGCC GCTAAAATTC GCCGNAACGG TGTTTTTAGT GGTATTAATT      60

GGGNAATTCT GTTGTAGCAG AAGATCCTTA TAGATATTTC GATTGGAATG TCACTTATGG     120

AACTATATAT CCTCTCGGAG TTCCTCAACA GGGAATTCTG ATTAATGGTC AATTTCCTGG     180

TCCTGATATC AACTCGGTCA CCAATGACAA TCTCGTTATC AATATCCACA ACAGCTTGGA     240

TGAACCTTTT CTACTTTCCT GGAACGGAAT ACAAAACAGA AGAAACTCAT TTGTAGATGG     300

AGTATATGGA ACAACATGCC CAATACCGCC AGGAGAAATA ACACATTCAA TCTACAAGTG     360

AAGGATCAAA TAGGGAGTTT CTATTACTTC CCATCTCTGC ATTCCACAAA GCTGCTGTGG     420

TTTTGGAGGG ATTAGGATNC TCAGCAGGCC TAGGATCCCC GTCCCTTTTC CGGACCCTGC     480
```

```
AAACGACTAC ACCATCCTCA TTGGAGATTG GTACAAAAAG AACCACACGG ACTTGAAAGC      540

AATTCTTGAC GGAGGCAGGA AGTTACCTTT NNCTGATGGC ATTCTTATCA ATGGTCGTGG      600

TCCTAATGGT GTTACATTCA CAGTCGATCA AGGGAAAACC TATAGATTGA GGATATCAAA     660

CGTTGGATTG CAAAATTCAT TGAATTTCCN CGTTGAAGGA CACAAAATGA CATTAGTTGA     720

AGTAGAGGGA ACACACACAT TGCAAACAAC TTATTCCTCA CTTGATGTCC ATGCTGGCCA     780

ATCTTACTCT GTCCTCATTA CAGCTAATCA AGAA                                  814

(2) INFORMATION FOR SEQ ID NO: 3:

(i) SEQUENCE CHARACTERISTICS:
         (A) LENGTH: 386 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: 3' END OF PE3

(xi) SEQUENCE DESCRIPTION: SEQ ID NO: 3:

ATACCTGATT CCCCGAACTG GTGCAGCAAT TTACCGAATA CGCGTCTGTT CTAGGTGTTA       60

ATTATAGGCA ATTCATTGAG ATTATATTCG AAAATAATGA GGATATCGTC CAGAGCTGGC     120

ATCTTGATGG CTACTCTTTT TGGGTTGTAG GGATGGATGG AGGCCAGTGG ACTCAAGCTA     180

GTAGGAACGG ATACAACCTC GTGATGCAGT TTCACGTTGC ACAACTCAGG TCTATCCCAA     240

GTCATGGACC GCGATATACA TGCATTGGAC AATGTAGGAA TGTGGAACCT GAGGACTGAA     300

TTCTGGGCNC NACAGTACCT CGGTCAACAA CTATAGATGA GAGTTTAGAC AGACTCAACC     360

TCAACCTCAT TGAGAGACGA ATATCC                                          386

(2) INFORMATION FOR SEQ ID NO: 4:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (vi) ORIGINAL SOURCE:
         (A) ORGANISM: N-TERMINAL PE3

(xi) SEQUENCE DESCRIPTION: SEQ ID NO: 4:

Glu Asp Pro Tyr Arg Tyr Phe Asp Trp
1               5

(2) INFORMATION FOR SEQ ID NO: 5:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: cDNA (vi) ORIGINAL SOURCE:
         (A) ORGANISM: OLIGO PROBE (xi) SEQUENCE DESCRIPTION: SEQ ID NO: 5:

GARGAYCCNT AYMGNTAYTT YGAYTGG                                          27
```

DNA ENCODING A PECTIN ESTERASE, CELLS AND PLANTS DERIVED THEREFROM

This application claims benefit of international application PCT/GB95/00367, filed Feb. 25, 1995.

This application relates to novel DNA constructs, plant cells containing the constructs and plants derived therefrom. In particular it relates to the modification of cell wall metabolism in fruit using DNA constructs.

The modification of plant gene expression has been achieved by several methods. The molecular biologist can choose from a range of known methods to decrease or increase gene expression or to alter the spatial or temporal expression of a particular gene. For example, the expression of either specific antisense RNA or partial sense RNA has been utilised to reduce the expression of various target genes in plants (as reviewed by Bird and Ray, 1991, Biotechnology and Genetic Engineering Reviews 9:207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al, 1992, Plant Molecular Biology, 19:69–87). Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences.

During fruit development and ripening, many biochemical changes occur that determine the composition and quality of the ripe fruit. The primary cell walls of the fruit are important constituents that influence the physical and eating properties of fresh fruit and processed products. Fruit cell walls are continually modified by both synthetic and degradative processes as the fruit expand and eventually ripen. Pectins are one of three classes of polysaccharide in the cell wall (the others being hemicelluloses and celluloses). Pectic polysaccharides in fruit consist mainly of an α1,4-galactuonan backbone with 2- and 2,4-linked rhamnosyl residues interspersed in the chain. The 2,4-linked rhamnosyl residues are thought to act as attachment points for β1,4-galactosyl and α1,5-linked arabinosyl residues (Seymour et al, 1990, Phytochemistry, 29:725–731). During ripening of fruit, there is major degradation of the pectin fraction. This involves pectin solubilisation and a reduction in the molecular weight of the galacturonan backbone. In addition, there is substantial de-methylation of the C6 position of galacturonic acid residues in high molecular weight pectin. The degree of esterification has been found to fall from 90% in mature green tomato fruit, to 35% in ripe fruit (Koch and Nevins, 1990, Plant Physiology, 91:816–822).

The de-methylation (de-esterification) of pectin is catalysed by pectin esterase (hereinafter called PE). In tomato fruit, PE activity is present throughout fruit development, with activity increasing two- to three fold during ripening (Hobson, 1963, Biochemical Journal, 86:358–365). In addition, PE activity is present in other plant tissues including leaves and roots.

Two major PE isoenzymes (hereinafter called PE1 and PE2 respectively) have been identified in tomato fruit (Tucker et al, 1982, J Sci Food Agric, 33:396–400). The ratio of these isoenzymes changes during ripening, with PE2 becoming the more dominant as ripening progresses.

PE2 is the major fruit isoenzyme and several closely related cDNA clones encoding PE2 have been isolated (Ray et al, 1988, Eur J Biochem, 174:119–124; Harriman et al, 1991, Plant Physiol, 97:80–87; International patent application publication number WO93/13212). It has been reported that at least three closely related genes encode proteins of the PE2 class. The modification of PE2 gene expression has been described. For example, expression of the PE2 isoenzymes has been reduced by up to 93% in transgenic tomato plants that express PE2 antisense RNA (Hall et al, 1993, Plant Journal, 3:121–129; Tieman et al, 1992, Plant Cell, 4:667–679). However, analysis of these plants indicated that a residual level of fruit PE activity (approximately 10%) was not susceptible to inhibition by the introduced PE2 antisense genes.

One of the objects of this invention is to provide a means to enable modification of that PE activity which cannot be modified using PE2-related DNA constructs.

In work leading to the present invention we have found that the PE isoenzyme originally identified as the single protein PE1 (Tucker et al, 1982, J Sci Food Agric, 33:396–400) actually comprises two different PE isoforms. These novel PE isoenzymes are hereinafter called PE1A and PE3.

According to the present invention, there is provided a DNA construct comprising a DNA sequence encoding a pectin esterase isoenzyme 3 (PE3) or a pectin esterase isoenzyme 1A (PE1A). These DNA sequences may be derived from cDNA, from genomic DNA or may be synthesised ab initio.

PE isoenzymes were isolated, purified and characterised from tomato fruit. Three isoenzymes were identified, and their molecular weights were estimated by gel permeation chromatography and by SDS-PAGE as follows:

PE1A 24.2 kD (chromatography) 33 kD (SDS-PAGE)
PE2 27.9 kD (chromatography) 32 kD (SDS-PAGE)
PE3 27.5 kD (chromatography) 46 kD (SDS-PAGE).

A chromatographically identical isoform to PE1A is the major PE isoenzyme in tomato leaves. It is also present in tomato fruit.

PE2 is present in developing and ripening fruit and represents approximately 85–90% of the ripe fruit PE. It has not been detected in tomato leaves.

PE3 is present in developing and ripening fruit and represents approximately 5% of the ripe fruit PE. It is barely detectable in tomato leaves.

The tomato PE3 isoenzyme has been purified to a single protein. N-terminal amino acid sequence analysis of purified PE3 gave the sequence: EDPYRYFDWXVT (SEQ ID NO 1). This sequence shows no homology to any published PE sequence. A degenerate oligonucleotide designed from this PE3 amino acid sequence was used to identify and isolate a cDNA clone (called R3.1) that encodes PE3. This clone was deposited on Jan. 20, 1994 under the terms of the Budapest Treaty at the National Collections of Industrial and Marine Bacteria (23 St. Machar Drive, Aberdeen, AB2 1RY, Scotland) and was given the accession number NCIMB 40610. The PE3 cDNA clone (R3.1, NCIMB 40610) was deposited as a bacteriophage lambda clone (lambda gt11 vector) using E coli Y1090r- as the host cell. The cDNA encoding PE3, as found in clone R3.1 (NCIMB 40610), may be sequenced according to known methods. SEQ ID NO 2 shows the 5' end sequence of the cDNA clone R3.1 (tomato pectin esterase 3 from tomato var Ailsa Craig). This sequence is 814 bases in length. SEQ ID NO 3 shows the 3' end sequence of the cDNA clone R3.1 which is 386 bases in length.

Additionally, the PE1A isoform has been purified and is distinguishable from the PE1 "isoenzyme" (actually an isoenzyme mixture). A DNA sequence encoding PE1A may be isolated as previously described for the PE3 sequence. Sequence determined by N-terminal or internal amino acid sequence analysis is used to design a degenerate oligonucleotide used for identification of a cDNA clone that encodes PE1A. The cDNA may be sequenced by known methods.

cDNA clones encoding PE3 or PE1A may also be obtained from the mRNA of tomatoes by methods similar to that described by Slater et al (1985, Plant Molecular Biology, 5:137–147). Sequences coding for the whole, or substantially the whole, of the mRNA produced by the PE3 gene or PE1A gene may thus be obtained. The cDNA so obtained may be sequenced according to known methods.

An alternative source of the PE3 or PE1A DNA sequence is a suitable gene encoding the appropriate PE isoenzyme. This gene may differ from the PE isoenzyme cDNA in that introns may be present. The introns are not transcribed into mRNA (or, if so transcribed, are subsequently cut out) Oligonucleotide probes or the cDNA clone may be used to isolate the actual PE3 or PE1A gene(s) by screening genomic DNA libraries. Such genomic clones may include control sequences operating in the plant genome. Thus it is also possible to isolate promoter sequences which may be used to drive expression of the PE isoenzymes or any other protein. These promoters may be particularly responsive to ripening events and conditions. PE3 or PE1A promoters may be used to drive expression of any target gene.

A further way of obtaining a PE3 or PE1A DNA sequence is to synthesise it ab initio from the appropriate bases, for example using the appropriate PE isoenzyme cDNA sequence as a guide.

It is clear that PE3-encoding and PE1A-encoding sequences may be isolated not only from tomato but from any suitable plant species. Alternative sources of suitable genes include bacteria, yeast, lower and higher eukaryotes.

The PE3-encoding sequences and the PE1A-encoding sequences may be incorporated into DNA constructs suitable for plant transformation. These DNA constructs may then be used to modify PE gene expression in plants. "Antisense" or "partial sense" or other techniques may be used to reduce the expression of the PE isoenzymes in developing and ripening fruit. The levels of the PE isoenzymes may also be increased; for example, by incorporation of additional PE isoenzyme genes. The additional genes may be designed to give either the same or different spatial and temporal patterns of expression in the fruit.

The overall level of PE activity and the relative activities of the individual PE isoenzymes affect the development and final form of pectins in the cell wall and thus determine certain characteristics of the fruit. Modification of PE iosenzyme activity can therefore be used to modify various aspects of fruit quality. For example, reducing isoenzyme activitiy may lead to:

a. Increased fruit firmness;
b. Improved resistance to mechanical damage during harvest and subsequent handling;
c. Improved texture of ripe fruit;
d. Improved resistance to fruit diseases;
e. Improved viscosity of processed fruit;
f. Improved solids content of processed fruit;
g. Improved resistance to chilling damage;
h. Other altered characteristics.

Increasing isoenzyme activity may lead to:

a. Modified fruit texture;
b. Modified processing properties;
c. Other altered characteristics.

Thus the activity levels of the PE isoenzymes may be either reduced or increased during development and ripening depending on the characteristics desired for the modified fruit.

The activity of the PE3 isoenzyme may be modified either individually or in combination with modification of the activity of the PE1A isoenzyme and/or the PE2 isoenzyme. The activity of PE1A may be modified either individually or in combination with modification of the activity of PE3 and/or PE2. In addition, the activities of the PE isoenzymes may be modified in combination with modification of the activity of other cell wall enzymes or enzymes involved in fruit ripening.

Use of the novel PE3 or PE1A constructs provides a method for modification of fruit characteristics comprising modification of the activity of PE isoenzymes which cannot be modified using PE2 constructs. The advantages of such a method include the following:

(1) with appropriate inhibitory constructs, pectin esterase activity can now be more completely suppressed: the absence of residual activity enhances the beneficial effects on fruit phenotype;

(2) the relative activities of the three different PE isozymes may be altered in various ways to give additional or enhanced effects on fruit phenotype.

Thus the invention provides a method which increases the efficiency and effectiveness of pectin esterase modification and/or extends the range of possible modifications. This provides a more efficient, effective and flexible method to modify fruit characteristics.

According to the present invention there is further provided a DNA construct comprising a DNA sequence homologous to some or all of a sequence encoding PE3 or PE1A under the control of a transcriptional initiation region operative in plants, so that the construct can generate RNA in plant cells.

The characteristics of fruit may be modified by transformation with a DNA construct according to the invention. The invention also provides plant cells containing such constructs; plants derived therefrom showing modified fruit characteristics; and seeds of such plants.

A DNA construct according to the invention may be an "antisense" construct generating "antisense" RNA or a "sense" construct (encoding at least part of the functional PE isoenzyme) generating "sense" RNA. "Antisense RNA" is an RNA sequence which is complementary to a sequence of bases in the corresponding mRNA: complementary in the sense that each base (or the majority of b ases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant g ene (or of a DNA sequence show ing substantial homology therewith). "Sense RNA" is an RNA sequence which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication WO91/08299) or to over-express the enzyme.

The constructs of the invention may be inserted into plants to regulate the production of pectin esterase isoenzymes encoded by genes homologous to sequences encoding either PE3 or PE1A. The constructs may be transformed into any dicotyledonous or monocotyledonous plant. Depending on the nature of the construct, the production of the enzyme may be increased, or reduced, either throughout or at particular stages in the life of the plant. Generally, as would be expected, production of the enzyme is enhanced only by constructs which express RNA homologous to the substantially complete endogenous PE isoenzyme mRNAs. Constructs containing an incomplete DNA sequence substantially shorter than that corresponding to the complete gene generally inhibit the expression of the gene and production of the enzymes, whether they are arranged to express sense or antisense RNA. Full-length antisense constructs also inhibit gene expression.

In a DNA construct according to the invention, the transcriptional initiation region may be derived from any plant-operative promoter. The transcriptional initiation region may be positioned for transcription of a DNA sequence encoding RNA which is complementary to a substantial run of bases in a mRNA encoding the PE3 or PE1A isoenzyme (making the DNA construct a full or partial antisense construct).

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable PE3-and PE1A-encoding sequences is described above. Sequences coding for the whole, or substantially the whole, of the appropriate PE isoenzyme may thus be obtained. Suitable lengths of this DNA sequences may be cut out for use by means of restriction enzymes. When using genomic DNA as the source of a partial base sequence for transcription it is possible to use either intron or exon regions or a combination of both.

To obtain constructs suitable for expression of the appropriate PE isoenzyme-related sequence in plant cells, the cDNA sequence as found in the PE isoenzyme cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the PE isoenzyme mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the mRNA. In constructs which express the functional PE isoenzyme, the whole of the coding region of the gene is linked to transcriptional control sequences capable of expression in plants.

For example, constructs according to the present invention may be made as follows. A suitable vector containing the desired base sequence for transcription (such as clone R3.1) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter and the tomato polygalacturonase gene promoter sequence (Bird et al, 1988, Plant Molecular Biology, 11:651–662) or other developmetally regulated fruit promoters. Suitable terminator sequences include that of the *Agrobacterium tumefaciens* nopaline synthase gene (the nos 3' end).

The transcriptional initiation region (or promoter) operative in plants may be a constitutive promoter (such as the 35S cauliflower mosaic virus promoter) or an inducible or developmentally regulated promoter (such as fruit-specific promoters), as circumstances require. For example, it may be desirable to modify pectin esterase activity only during fruit development and/or ripening. Use of a constitutive promoter will tend to affect pectin esterase levels and functions in all parts of the plant, while use of a tissue specific promoter allows more selective control of gene expression and affected functions (pectin de-esterification). Thus in applying the invention (for example, to tomatoes) it may be found convenient to use a promoter that will give expression during fruit development and/or ripening. Thus the antisense or sense RNA is only produced in the organ in which its action is required. Fruit development and/or ripening-specific promoters that could be used include the ripening-enhanced polygacturonase promoter (International Patent Publication Number WO92/08798), the E8 promoter (Diekman & Fischer, 1988, EMBO, 7:3315–3320) and the fruit specific 2A11 promoter (Pear et al, 1989, Plant Molecular Biology, 13:639–651).

Pectin de-esterification (and hence fruit ripening characteristics) may be modified to a greater or lesser extent by controlling the degree of the appropriate PE isoenzyme's sense or antisense mRNA production in the plant cells. This may be done by suitable choice of promoter sequences, or by selecting the number of copies or the site of integration of the DNA sequences that are introduced into the plant genome. For example, the DNA construct may include more than one DNA sequence encoding the PE isoenzyme or more than one recombinant construct may be transformed into each plant cell.

The activity of the PE3 isoenzyme may be separately modified by transformation with a suitable DNA construct comprising a PE3-encoding DNA sequence. The activity of the PE1A isoenzyme may be separately modified by transformation with a suitable DNA construct comprising a PE1A-encoding DNA sequence. In addition, the activity of both PE3 and PE1A may be simultaneously modified by transforming a cell with two separate constructs: the first comprising a PE3-encoding sequence and the second comprising a PE1A-encoding sequence. Alternatively, a plant cell may be transformed with a single DNA construct comprising both a PE3-encoding sequence and a PE1A-encoding sequence.

It is also possible to modify the activity of the PE3 and/or PE1A isoenzyme while also modifying the activity of one or more other enzymes. The other enzymes may be involved in cell metabolism or in fruit development and ripening. Other cell wall metabolising enzymes that may be modified in combination with PE3 and/or PE1A include but are not limited to: PE2, polygalacturonase, β-galactanase, β-glucanase. Other enzymes involved in fruit development and ripening that may be modified in combination with PE3 and/or PE1A include but are not limited to: ethylene biosynthetic enzymes, carotenoid biosynthetic enzymes including phytoene synthase, carbohydrate metabolism enzymes including invertase.

Several methods are available for modification of the activity or the PE3 and/or PE1A isoenzymes in combination with other enzymes. For example, a first plant may be individually transformed with a PE3 and/or PE1A construct and then crossed with a second plant which has been individually transformed with a construct encoding another enzyme. As a further example, plants may be either consecutively or co-transformed with PE3 and/or PE1A constructs and with appropriate constructs for modification of the activity of the other enzyme(s). An alternative example is plant transformation with a PE3 and/or PE1A construct which itself contains an additional gene for modification of the activity of the other enzyme(s). The PE3 and/or PE1A constructs may contain sequences of DNA for regulation of the expression of the other enzyme(s) located adjacent to the PE isoenzyme sequences. These additional sequences may be in either sense or antisense orientation as described in International patent application publication number WO93/23551 (single construct having distinct DNA regions homologous to different target genes). By using such methods, the benefits of modifying the activity of the PE isoenzymes may be combined with the benefits of modifying the activity of other enzymes. A particular application is the co-inhibition of PE3 and/or PE1A with the third isoenzyme PE2 in order to completely suppress pectin esterase activity in the fruit.

A DNA construct of the invention is transformed into a target plant cell. The target plant cell may be part of a whole plant or may be an isolated cell or part of a tissue which may be regenerated into a whole plant. The target plant cell may be selected from any monocotyledonous or dicotyledonous plant species. Suitable plants include any fruit-bearing plant (such as tomatoes, mangoes, peaches, apples, pears, strawberries, bananas, melons). For any particular plant cell, the PE3 and/or PE1A sequence used in the transformation construct may be derived from the same plant species, or may be derived from any other plant species (as there will be sufficient sequence similarity to allow modification of related isoenzyme gene expression).

Constructs according to the invention may be used to transform any plant using any suitable transformation technique to make plants according to the invention. Both monocotyledonous and dicotyledonous plant cells may be transformed in various ways known to the art. In many cases such plant cells (particularly when they are cells of dicotyledonous plants) may be cultured to regenerate whole plants which subsequently reproduce to give successive generations of genetically modified plants. Any suitable method of plant transformation may be used. For example, dicotyledonous plants such as tomato and melon may be transformed by Aqrobacterium Ti plasmid technology, such as described by Bevan (1984, Nucleic Acid Research, 12:8711–8721) or Fillatti et al (Biotechnology, July 1987, 5:726–730). Such transformed plants may be reproduced sexually, or by cell or tissue culture.

The invention will now be described by way of example only, with reference to the SEQUENCE LISTING in which:

SEQ ID NO 1 shows twelve residues of the N-terminal amino acid sequence of PE3;

SEQ ID NO 2 shows the 5' end cDNA sequence of PE3 (clone R3.1);

SEQ ID NO 3 shows the 3' end cDNA sequence of PE3 (clone R3.1);

SEQ ID NO 4 shows nine residues of the N-terminal amino acid sequence of PE3;

SEQ ID NO 5 shows the nucleotide sequence of the oligonucleotide probe RJW17.

EXAMPLE 1

Extraction of Pectin Esterase Iso-Enzymes from Tomato Fruit

Total cell wall protein was extracted from ripe tomato pericarp by sequential homogenization in water and 1M NaCl as described in Tucker et al (1980, Eur J Biochem, 112:119–124). The extract was dialysed against 0.15M NaCl in 0.2M NaOAc buffer (pH6.0) at 4° C. for 12 hr prior to loading on a 5×80 cm DEAE-Sephadex A-50 column that had been pre-equilibrated in the same buffer. 12 ml fractions were collected and assayed for protein and pectin esterase activity. A major (fractions 55 to 70) and a minor (fractions 25 to 45) peak of pectin esterase activity were identified. These were combined as separate pools which were ultrafiltrated (Amicon PM-10 membrane) to 6ml.

The major peak of pectin esterase activity contained the PE2 isoenzyme that had been previously purified and characterised (Tucker et al, 1982, J Sci Food Agric, 33:396–400). The minor peak contained pectin esterase isoforms that had not previously been purified.

EXAMPLE 2

Purification of PE1A and PE3 Isoforms

The concentrated pool from the minor peak (fractions 25 to 45) of pectin esterase activity (Example 1) was further purified using High Resolution Liquid Chromatography (Bio-Rad 800/netware system, model 1740 with twin pumps and a 280 nm detector).

The pool was applied to a Bio-Sil TSK-250 gel filtration column (600×7.5mm) and eluted in 10 mM $Na_2HPO_4$/$NaH_2PO_4$ (pH6.0), 0.15M NaCl at a flow of 1 ml/min. 1 ml fractions were collected and one peak of pectin esterase activity was identified. The fractions corresponding to this peak of activity were concentrated by ultrafiltration to approximately 1 ml prior to loading on to a Bio-Rad MA7S cation exchange column (50×7.8 mm). The column was equilibrated with 10 mM $Na_2HPO_4$/$NaH_2$ $PO_4$ (pH6.7) and the sample was eluted with a linear NaCl gradient (0–0.25M) applied at 1.5 ml/min over 10 minutes. Two peaks of pectin esterase activity were identified: PE1A (retention time—10.88 min); PE3 (retention time—8.0 min). Using an identical purification protocol, PE2 has a retention time of 6.8 min.

EXAMPLE 3

Isolation of Pectin Esterase 3 (PE3) Peptide and N-terminal Sequence Analysis

In order to obtain almost pure PE1A and PE3 isoenzymes, three repeats of purification on the MA7S cation exchange column were carried out in order to remove associated protein. SDS-PAGE combined with silver staining was used to confirm that the proteins had been purified to homogeneity. Molecular weights of PE1A and PE3 were estimated to be 33000 and 46000 respectively. Under the same conditions, PE2 had an apparent molecular weight of 32000.

The N-terminal amino acid sequence of PE3 purified from the MA7S column was determined using commercially available procedures. The first 2 amino acids were determined as: EDPYRYFDWXVT (SEQ ID NO 1). The N-terminal or partial internal sequence of PE1A is obtained by similar procedures.

EXAMPLE 4

Identification, Isolation and Characterisation of a cDNA Clone Encoding Tomato Fruit Pectin Esterase 3 (PE3)

The determined N-terminal amino acid sequence of PE3 (SEQ ID NO 4) was used to design a degenerate oligonucleotide for use as a probe to detect a cDNA clone encoding PE3. The sequence of the oligonucleotide probe RJW17 (SEQ ID NO 5) was as follows:

```
Amino acid      E  D  P  Y  R  Y  F  D  W
Oligonucleotide GAAGATCCTTATAGTTATTTTGATTGG
                G  C  C CC  C  C  C
                      A     A
                      G     G
```

The oligonucleotide was end labelled with $^{32}P$ and used to screen 100,000 plaques from a tomato (var Ailsa Craig) ripe fruit cDNA library. The filters were hybridised to the oligo at 32° C. and washed in 6×SSC, 0.5% SDS at the same temperature. After autoradiography, 5 hybridising plaques were identified. After picking and re-plating the 5 hybridising plaques, three of the plaques (R3.1, R4.1, R5.1) continued to hybridise to the oligonucleotide probe. R3.1 and R4.1 contained a 1.4 kb EcoRI fragment, whereas R5.1 contained a 1.6kb EcoRI fragment.

The insert of the insert in R3.1 was partially determined by direct sequencing of purified phage DNA. Sequence encoding the determined N-terminal amino acid sequence of PE3 was identified.

EXAMPLE 5

Construction of Antisense RNA Vectors with the CaMV 35S Promoter

A vector is constructed using the sequences corresponding to a fragment of the insert of a PE3 cDNA (isolated as shown in example 4). This fragment is synthesised by polymerase chain reaction using synthetic primers. The ends of the fragment are made flush with T4 polymerase and it is cloned into the vector pJR1 which has previously been cut with SmaI. pJR1 (Smith et al, 1988, Nature, 334:724–726) is a Bin19 (Bevan, 1984, Nucleic Acids Research, 12:8711–8721) based vector, which permits the expression of the antisense RNA under the control of the CaMV 35S promoter. This vector includes a nopaline synthase (nos) 3' end termination sequence.

Alternatively a vector is constructed using a restriction fragment obtained from a PE3 cDNA and cloned into the vectors GA643 (An et al, 1988, Plant Molecular Biology Manual A3: 1–19) or pDH51 (Pietrzak et al, 1986, Nucleic Acids Research, 14:5875–5869) which has previously been cut with a compatible restriction enzyme(s). A restriction fragment from the PE3/pDH51 clone containing the promoter, the PE3 fragment and other pDH51 sequence is cloned into SLJ44026B or SLJ44024B (Jones et al, 1990, Transgenic Research, 1) or Bin19 (Bevan, 1984, Nucleic Acids Research, 12:8711–8721) which permits the expression of the antisense RNA under control of the CaMV 35S promoter.

After synthesis of the vector, the structure and orientation of the sequences are confirmed by DNA sequence analysis.

EXAMPLE 6

Construction of Antisense RNA Vectors with a Fruit Enhanced Promoter

The fragment of the PE3 cDNA that was described in Example 5 is also cloned into the vector pJR3. pJR3 is a Bin19 based vector, which permits the expression of the antisense RNA under the control of the tomato polygalacturonase (PG) promoter. This vector includes approximately 5 kb of promoter sequence and 1.8 kb of 3' sequence from the PG promoter separated by a multiple cloning site.

After synthesis, vectors with the correct orientation of the PE3 sequences are identified by DNA sequence analysis.

Alternative fruit enhanced promoters (such as E8 or 2A11) are substituted for the polygalacturonase promoter in pJR3 to give alternative patterns of expression.

EXAMPLE 7

Construction of Truncated Sense RNA Vectors with the CaMV 35S Promoter

The fragment of the PE3 cDNA that was described in Example 5 is also cloned into the vectors described in Example 5 in the sense orientation.

After synthesis, the vectors with the sense orientation of the PE3 sequence are identified by DNA sequence analysis.

EXAMPLE 8

Construction of Truncated Sense RNA Vectors with Fruit-Enhanced Promoter

The fragment of the PE3 cDNA that was described in Example 5 is also cloned into the vector pJR3 in the sense orientation.

After synthesis, the vectors with the sense orientation of the PE3 sequence are identified by DNA sequence analysis.

Alternative fruit enhanced promoters (eg E8 or 2A11) are substituted for the polygalacturonase promoter in pJR3 to give alternative patterns of expression

EXAMPLE 9

Construction of a PE3 Over-Expression Vector Using the CaMV35S Promoter

The complete sequence of a PE3 cDNA containing a full open-reading frame is inserted into the vectors described in Example 5.

EXAMPLE 10

Construction of a PE3 Over-Expression Vector Using a Fruit-Enhanced Promoter The complete sequence of a PE3 cDNA containing a full open-reading frame is inserted into pJR3 or alternatives with different promoters.

EXAMPLE 11

Generation of Transformed Plants

Vectors are transferred to *Agrobacterium tumefaciens* LBA4404 (a micro-organism widely available to plant biotechnologists) and are used to transform tomato plants. Transformation of tomato stem segments follow standard protocols (e.g. Bird et al, 1988, Plant Molecular Biology, 11:651–662). Transformed plants are identified by their ability to grow on media containing the antibiotic kanamycin. Plants are regenerated and grown to maturity. Ripening fruit are analyzed for modifications to their ripening characteristics.

EXAMPLE 12

Analysis of Transgenic Plants

A partial sense construct containing a 1.5 kb fragment of the PE3 clone R3.1 was made as described in Example 7. The construct was transformed into tomato (variety Ailsa Craig). Aprroximately twenty transformants have been generated; PCR analysis has shown that the majority of these transformants contain the PE3 partial sense construct. The transgenic plants produced fruit which is being assayed for PE3 activity.

We claim:

1. A DNA construct comprising a DNA sequence encoding a tomato pectin esterase isoenzyme selected from the group consisting of pectin esterase isoenzyme 3 and pectin esterase isoenzyme 1A.

2. A DNA construct as claimed in claim 1 in which the DNA sequence encodes pectin esterase isoenzyme 3 encoded by the insert in the R3.1 clone deposited at the National Collections of Industrial and Marine Bacteria under the accession number NCIMB 40610.

3. A DNA construct comprising at least 35 bases of a DNA sequence selected from the group consisting of SEQ ID NO 2 and SEQ ID NO 3.

4. A DNA construct as claimed in claim 1 in which the DNA sequence encodes an N-terminal amino acid sequence selected from the group consisting of SEQ ID NO 1 and SEQ ID NO 4.

5. A method of isolating a DNA molecule comprising a DNA sequence encoding a pectin esterase isoenzyme 3 in which said DNA sequence is identified by being hybridized to a DNA probe comprising SEQ ID NO 5 at 32° C. and washed in 6×SSC and 0.5% SDS at 32° C.

6. A DNA construct as claimed in claim 3 in which the DNA sequence is selected from the group consisting of SEQ ID NO 2 and SEQ ID NO 3.

7. A DNA construct as claimed in any one of claims 1,2,3 or 4 in which the DNA sequence is in sense or antisense orientation and is under the control of a transcriptional initiation region operative in plants, so that the construct can generate RNA in plant cells.

8. A plant cell transformed with a DNA construct as claimed in claim 7.

9. A plant derived from a plant cell as claimed in claim 8.

* * * * *